United States Patent [19]
Toledano

[11] Patent Number: 5,783,401
[45] Date of Patent: Jul. 21, 1998

[54] IMMUNOENZYMATIC DETECTION DEVICE

[75] Inventor: Jacques Toledano, Paris, France

[73] Assignee: Quidel Corporation, San Diego, Calif.

[21] Appl. No.: 269,637

[22] Filed: Jul. 1, 1994

Related U.S. Application Data

[63] Continuation of Ser. No. 782,161, Oct. 24, 1991, abandoned, which is a continuation of Ser. No. 368,329, filed as PCT/FR88/00493 Oct. 15, 1988, abandoned.

[30] Foreign Application Priority Data

Oct. 5, 1987 [FR] France ..................... 87 13879

[51] Int. Cl.$^6$ ........................................... G01N 33/53
[52] U.S. Cl. ............... 435/7.9; 435/7.92; 435/7.93; 435/7.94; 435/7.95; 435/970; 436/518; 436/524; 436/525; 436/526; 436/532; 436/533; 436/534; 436/535; 427/2.13
[58] Field of Search .................. 422/56–58, 101; 435/5, 7.9, 7.92–7.95, 7.24, 805, 810, 970, 973, 974; 436/518, 524–526, 532–535, 807, 810; 427/2.13

[56] References Cited

U.S. PATENT DOCUMENTS

| | | | |
|---|---|---|---|
| 4,138,394 | 2/1979 | Sakakibara et al. | 435/24 |
| 4,258,001 | 3/1981 | Pierce et al. | 422/56 |
| 4,366,241 | 12/1982 | Tom et al. | 435/7.92 |
| 4,446,232 | 5/1984 | Liotta | 435/7.9 |
| 4,459,358 | 7/1984 | Berke | 436/178 |
| 4,587,102 | 5/1986 | Nagatomo et al. | 422/56 |
| 4,608,231 | 8/1986 | Witty et al. | 422/61 |
| 4,752,572 | 6/1988 | Sundberg et al. | 435/7.9 |
| 4,774,174 | 9/1988 | Giegel et al. | 436/810 X |
| 4,803,154 | 2/1989 | Uo et al. | 435/7.9 |
| 4,923,680 | 5/1990 | Nelson | 422/58 |
| 5,079,141 | 1/1992 | Niskanen et al. | 435/7.34 |
| 5,217,905 | 6/1993 | Marchand et al. | 436/518 |

FOREIGN PATENT DOCUMENTS

| | | | |
|---|---|---|---|
| 0191640 | 8/1906 | European Pat. Off. | 435/7.9 |
| 0133700 | 3/1985 | European Pat. Off. | 422/56 |
| 0200540 | 11/1986 | European Pat. Off. | 435/17 |
| 0212989 | 3/1987 | European Pat. Off. | 435/7.9 |
| 0231830 | 8/1987 | European Pat. Off. | 435/7.9 |
| 0236768 | 9/1987 | European Pat. Off. | 422/56 |
| 80/02077 | 10/1980 | WIPO | 436/514 |
| 86/04683 | 8/1986 | WIPO | 435/7.9 |

Primary Examiner—Carol A. Spiegel
Attorney, Agent, or Firm—Townsend and Townsend and Crew LLP

[57] ABSTRACT

A device for detecting the presence of substances, particularly biological materials, contained in a liquid sample is formed of a series of layers of film materials. A first film has a cut-out which forms an upper reservoir for receiving the liquid sample. A first reagent is provided in the upper reservoir capable of reacting with a substance possibly contained in the liquid sample. A first membrane is situated at the base of the upper reservoir and is made of a material which is temporarily impermeable so that the liquid sample is temporarily retained in the upper reservoir in contact with the first reagent, but after awhile the membrane becomes permeable and allows the liquid to pass. A second film has a cut-out which forms a median reservoir positioned for receiving the liquid passing through the first membrane. A second reagent is provided in the median reservoir capable of reacting with a predetermined substance. A second membrane is situated at the base of the second reservoir and is similarly made of a material which is temporarily impermeable, but which later becomes permeable. A third film has a cut-out forming a lower reservoir positioned for receiving the liquid passing through the second membrane and a third reagent is provided in the lower reservoir and is formed of a material capable of developing a color reaction by contact with the liquid which reaches the lower reservoir after passing through the second membrane.

20 Claims, 1 Drawing Sheet

IMMUNOENZYMATIC DETECTION DEVICE

"This is a continuation of copending application Ser. No. 07/782,161, now abandoned, filed on Oct. 24, 1991 which is a continuation of application Ser. No. 07/368,329 now abandoned filed on Jan. 17, 1990 which is a 371 filing of international Application PCT/FR88/00493 filed on Oct. 5, 1988 and which designated the U.S."

BACKGROUND OF THE INVENTION

The present invention relates to a device for detecting the presence, in a biological medium, of chemical or biological substances, even present in very small concentrations, of the order of a nanogram per milliliter. The invention relates more particularly to rapid biological tests using the antigen-antibody reaction to reveal, by coloration of a substrate, the presence of substances which it is desired to detect.

Diagnosis strips have been known for a long time for carrying out detection tests in urine. Strips are also known comprising a square of cellulose for determining the quantity of glucose from a drop of blood deposited on the cellulose square, held for a minute thereon, then washed so as to read the coloured reaction.

Immuno-enzymatic detection devices also exist using antigens or antibodies, but requiring, on the one hand, staff for taking blood samples, and handling and, on the other hand, using a complex, expensive and especially very time consuming system (three hours because of the repeated washing following periods of incubation of half an hour between each phase).

The device of the present invention overcomes these drawbacks and makes available for patients, doctors, small care centres, transfusion centres, emergency services, etc . . . a whole range of high speed tests, since this device, which only requires a drop of liquid to be analysed, makes diagnosis possible in the few following minutes without any human intervention, by simply reading the coloration of a substrate pellet situated in the lower part of the device, whence its reduced cost and great ease of use.

SUMMARY OF THE INVENTION

The present invention provides a device for detecting the presence of substances in a liquid or solid biological medium, even when they are present in very small concentrations, of the order of a nanogram per milliliter, which device is characterized in that it comprises, in combination:

- a transparent or opaque plastic material film cut out so as to form an upper reservoir for receiving a drop of biological medium to be analysed,
- a first filter membrane, which is temporarily impermeable in the presence of a reaction sample; situated at the base of the reservoir and whose upper face carries a thin layer of a reagent (A), intended to react with the drop of biological medium to be analysed,
- a second transparent or opaque plastic material film cut out so as to form a median reservoir for receiving the liquid coming from the passage of the drop through the first said filter membrane, which median reservoir contains a reagent (B) capable of reacting with said liquid,
- a second membrane which is temporarily impermeable, also a filter, situated at the base of the median reservoir and through which the liquid passes after its contact with the reagent (B) in said median reservoir,
- a third transparent or opaque plastic material film cut out so as to form a lower reservoir which contains an appropriate carrier for a reagent (C) which, by contact with the liquid which reaches the lower reservoir after passing through the membrane, has a coloration adapted to indicate the presence or absence of the substance sought, in the biological medium analysed.

In an advantageous embodiment of the device of the present invention, the reagent (A) is an antibody or an antigen marked by an appropriate marker and preferably lyophilized. The reagent (B) is, formed by microspheres made from an appropriate material and coated with an antigen or an antibody; the reagent (C) is a substrate capable of reacting with the marker of reagent (A) so as to give, a coloration in contact with the reagent (A).

In another advantageous embodiment of the device of the present invention, the reagent (A) is formed by an unmarked antibody present in a predetermined amount and the device comprises, following the upper reservoir, a reagent (D) formed by marked antibodies contained in liposomes.

In yet another advantageous embodiment of the device of the present invention, the reagent (C) is carried by an appropriate carrier such more particularly as a cellulose pellet or the like.

In another advantageous embodiment of the device of the present invention, it comprises a plurality of reservoirs cut out from each film so as to permit the simultaneous detection of several different substances.

In yet another advantageous embodiment of the device of the present invention, it is equipped with additional films.

In an advantageous embodiment of the device of the present invention, the reagent (A) is formed by a plurality of different antibodies or antigens specific of a disease and the reagent (C) comprises a plurality of substrates capable of reacting with one or more of the markers which form the reagent (A) so as to give, one or more colorations.

In another advantageous embodiment of the device of the present invention, the filter membranes are made from gelatin and glass fibres.

Besides the above arrangements, the invention comprises yet other arrangements which will be clear from the following description.

BRIEF DESCRIPTION OF THE DRAWINGS

The invention will be better understood from the complement of description which follows, with reference to the accompanying drawing, in which.

Figure 1:
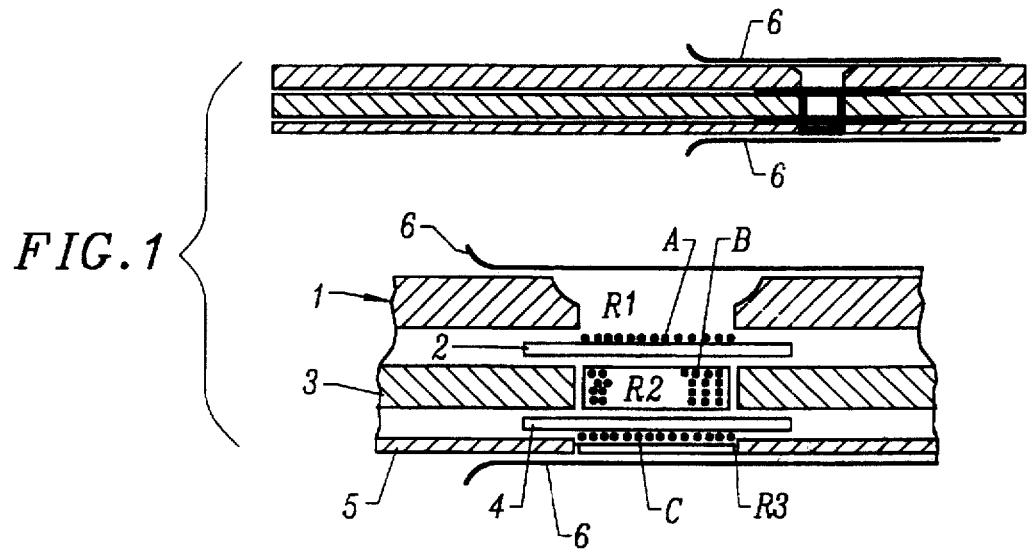
FIG. 1 is a longitudinal sectional view of the device of the invention.
Figure 2:
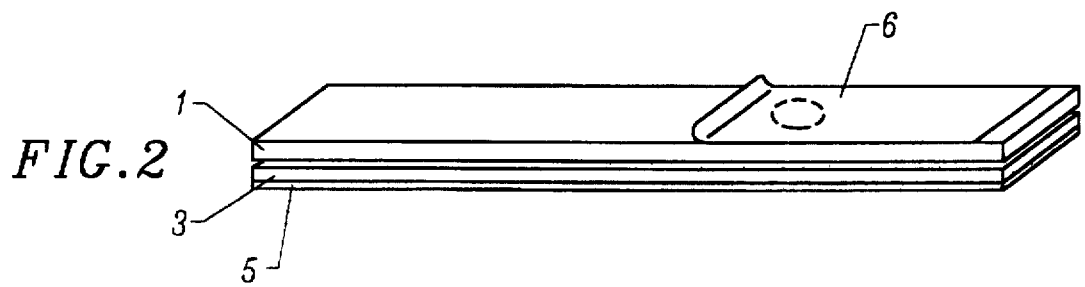
FIG. 2 is a perspective view thereof.
Figure 3:
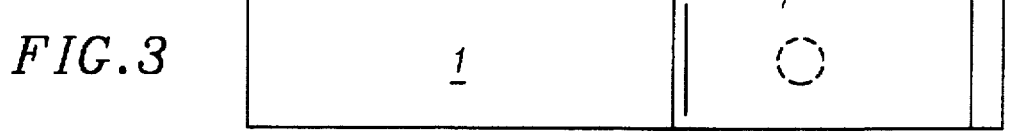
FIG. 3 is a top view thereof.
Figure 4:
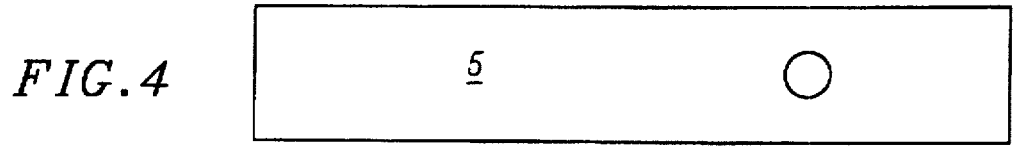
FIG. 4 is a bottom view.

It should however be understood that this drawing and the corresponding descriptive parts are given solely by way of illustration of the object of the present invention, of which they form in no wise a limitation.

DESCRIPTION OF THE ILLUSTRATED EMBODIMENT

The device shown in the drawing is formed of superimposed elements 1 to 5, all of the same length, e.g. 100 mm, and of the same width, e.g. 20 mm, all having at the same position one or more cut-outs (reservoirs R1, R2 and R3), which may be circular, with a diameter of 5 to 20 mm depending on the required diagnoses, but of different thicknesses, namely respectively from top to bottom:

1) A transparent or opaque plastic material film 1, 0.5 to 5 mm thick, for receiving at R1 the drop of liquid to be analysed.

2) A gelatin and glass fibre membrane 2, of a thickness from 0.5 to 1.5 mm, supporting on its upper face a thin reagent layer (A) for reacting immediately with the drop of liquid to be analysed.

3) A transparent or opaque plastic material film 3, 1 to 5 mm thick, receiving at R2 the liquid coming from filtration of the drop through the membrane 2, which liquid will enter into contact with the reagent (B) in reservoir (R2).

4) A membrane also made of gelatin and glass fiber, for filtering the liquid after its contact with the reagent (B).

5) A transparent or opaque plastic material film 5, 0.5 to 2 mm in thickness, whose cut-out forms the reservoir R3 containing a cellulosepellet-or any other carrier capable of containing the reagent (C). The latter in contact with the liquid coming from the filter membrane 4 has a different coloration depending on whether the substance sought is present or not in the liquid to be analysed. The reaction is then read by simply turning over the device after one to three minutes depending on the different analyses.

6) An opaque protective adhesive film 6, which covers R1 on the top and R3 on the bottom.

The reagent (A) is formed by a lyophilized antibody or antigen, marked by any suitable marker, such as enzymes, fluorescence or radioactivity, etc . . .

The membrane 2 is made from gelatin on glass fibres, with a porosity varying from 0.2 to 50 microns depending on the desired diagnoses, and supports the reagent (A) on its upper face.

The membrane 4 is also made from gelatin on glass fibres, of a porosity between 0.2 and 50 microns.

The reagent (B) is formed by microspheres of a diameter varying from 10 to 250 microns, made from iron or any other metal, metal alloys, polyacrylamide or any other material, coated with hydroxyapatite and protein A for solidly fixing an antigen or an antibody after agitation. They are then placed in contact for one to six hours with ethanolamine so as to block all the amine sites and thus avoid any other chemical reaction than the one concerning the antigen-antibody.

The reagent (C) is a substrate of the marker of reagent (A); for example, in the case where the antigen or antibody is marked by an enzyme, if this enzyme is a peroxydase, the substrate will be 3—3' 5—5' tetramethylbenzidine for a blue coloration or oxyphenyldiamine for an orange coloration.

In a variant, several reservoirs may exist for detecting several different substances. For example it is advantageous for the hepatitis diagnosis test to associate a rapid evaluation of the transaminases. Similarly, in the case of a heart attack, evaluation of the cardiac enzyme rate gives a very precious indication on the prognosis and the seriousness of the lesions. Similarly also, the sero positivity of AIDS not being sufficient, it may be completed on the same strip by an immunological test capable of indicating the quality and number of lymphocytes T, and thus to permit the follow-up of sero positives.

In a variant of carrying out the reservoirs, they may be square, rectangular, oval, etc . . .

In another variant, the number of films may be greater than or less than the three described above.

The device of the present invention makes it possible to track down numerous diseases involving an agent (the antigen) and the reaction of the organism to this agent, namely the revelation and detecting of the antibodies against this agent from a drop of any liquid coming from the human body (blood, serum, plasma, urine, saliva, tears, cerebraspinal fluid, ureteral and vaginal humours, mother's breast milk, liquids swabbed during an operation, or from organs to be grafted, for detecting AIDS for example) etc . . .

Detection may also be made from fragments of any solids previously solubilized or simply agitated with a little water.

The detection device of the present invention also applies to veterinary medicine for tracking down infections or detecting of hormones for example.

It also applies to the food processing industry whenever it is a question of tracking down or detecting of all chemical substances (e.g. toxins) or any biological substance (germs, vitamin content for example).

The invention also applies to agriculture for microdetermination.

It also applies, in a more general context, to everything concerning microdetermination required for investigations, research, water treatment, ecology (diagnosis of diseases in disappearing species, for example).

The device of the present invention is capable of detecting the antigen rate of certain cancers, solving the dramatic problem of treated patients, in whom it is practically impossible to know sufficiently early if they will have a relapse, metastases, whereas the device of the present invention makes it possible to reveal them by the coloured reaction as soon as the antigen rate exceeds a certain limit.

It is also intended for the early and rapid detection of numerous diseases (syphilis, AIDS, hepatitis . . . ) and obtaining rapid biological indications such as blood groupings, the evaluation of circulating enzymes and finally the diagnosis of diseases difficult to determine (rabies, paludism, . . . ).

A non exhaustive list is given hereafter of the infections capable of being diagnosed by means of the device of the present invention, classed as follows:

I—Diagnosis of viral diseases.

II—Diagnosis of microbial diseases.

III—Enzymatic detecting.

IV—Auto-immune illnesses and Alzheimer's sclerosis

V—Rapid blood groupings.

VI—Tracking down cancers.

VII—Detecting of circulating medicaments.

VIII—Detection of allergens.

Diagnosis of allergies.

IX—Detecting of membrane receptors.

X—Detecting of hormones.

XI—Various determinations (such as detection of the anions and cations of the ionogram metals and, generally, all elements of Mendeleieff's classification).

The detection device of the present invention operates as follows:

1) A drop of liquid-is deposited in reservoir R1.

2) After a minute, the serum has reacted with the reagent (A) and the gelatin of the first temporarily impermeable membrane 2 dissolves to let the serum filter through the glass fibre.

3) The serum enters into contact at R2 with the microspheres coated with the reagent (B). After a minute, the gelatin of the second temporarily impermeable membrane 4 dissolves to let the serum filter through the glass fibre and;

4) Arrival of the serum on the reagent (C) in reservoir R3 so as to show immediately a coloration depending on the result.

In the case of searching for antigens:

Positive reaction: the antigen is bonded to the antibody (A) at R1, passes through R2 without being retained by the spheres and arrives at R3 to colour the substrate.

Negative reaction: no antigen: the marked antibody (A) will be retained by the antigen of the microspheres and will therefore not colour the substrate.

In the case of searching for antibodies:

Same principle except that (A) will be a marked antigen and an antibody is fixed on the microspheres for retaining this marked antigen in the absence of antibodies in the serum.

Semi-quantitative detection:

At (A) unmarked antibodies are fixed, fixing for example 10 ng/ml of antigen. If the serum contains more, it will be later fixed on marked antibodies enclosed in liposomes which open after a minute. Same principle for the semi-quantitative titration of antibodies.

The device of the present invention:

because of its structure avoids the different washing steps which are usual in immunology and so provides a considerable time saving over the other tests;

makes it possible to have biological information of first importance from a drop of blood taken from a finger, and so to be able to be used in the absence of specialized nursing staff and in the absence of a laboratory;

provides a great flexibility in use since the same test may detect a substance in a drop of urine or in a drop of milk or in a solid previously solubilized;

makes it possible to detect several different substances with the same drop of blood by simply associating, in the above described reservoirs, the reagents corresponding to said substances. If the test is positive, it is because at least one of the substances sought is present in the drop examined. Thus, for example, different cancer markers may be placed in the same test (digestive for example: ACE for the colon, C19-9 for the pancreas, etc . . . ).Since it is improbable that the subject has several different cancers, if the test is positive, it directs the doctor towards the digestive sphere and then to make separate tests for each cancer and each member so as to thus localize a beginning tumour.

Similarly, before a surgical operation on the operating table, the surgeon or anaesthetist may use a test in which the microspheres of the reagent (B) are covered either with different antigens (HIV, HTLV, hepatitis, etc . . . ), or a test with a percentage of spheres marked with HIV, another portion with HTLV, etc . . . , so that a drop of blood, in a single test with the same device, may give indications of the highest importance.

As is clear from the foregoing, the invention is in no wise limited to those of its embodiments and modes of application which have just been described more explicitly; it embraces, on the contrary, all variants thereof which may occur to the mind of a technician skilled in the matter without departing from the scope or spirit of the present invention.

I claim:

1. A device for detecting the presence of at least one analyte in a liquid sample comprising:

(a) an upper reservoir for receiving said liquid sample comprising:

(i) a first film having a first cut-out which defines the lateral walls of said upper reservoir, (ii) a first membrane comprised of gelatin and glass fibers situated at the base of said first cut-out thereby forming the bottom of said upper reservoir, wherein said first membrane is capable of retaining said liquid sample in said upper reservoir for a predetermined period of time until contact with said liquid sample dissolves said gelatin thereby permitting liquid in said upper reservoir to flow into a median reservoir, and (iii) a predetermined amount of a first reagent provided in said upper reservoir, said first reagent selected from the group consisting of (1) a conjugate of said at least one analyte and an enzyme, a fluorescent or a radioactive label, and (2) a conjugate of an antibody which specifically binds said at least one analyte and an enzyme, a fluorescent or a radioactive label;

(b) said median reservoir comprising:

(i) a second film having a second cut-out which defines the lateral walls of said median reservoir positioned for receiving the upper reservoir liquid passing through said first membrane, (ii) a second membrane comprised of gelatin and glass fibers situated at the base of said second cut-out thereby forming the bottom of said median reservoir, wherein said second membrane is capable of retaining said upper reservoir liquid in said medium reservoir for a predetermined period of time until contact with said upper reservoir liquid dissolves said gelatin thereby permitting liquid in said median reservoir to flow into a lower reservoir, and (iii) a predetermined amount of a second reagent provided in said median reservoir, said second reagent selected from the group consisting of microspheres coated with said at least one analyte and microspheres coated with said antibody; and (c) said lower reservoir comprising:

(i) a third film having a third cut-out which defines the lateral walls of said lower reservoir positioned for receiving the median, reservoir liquid passing through said second membrane, (ii) an adhesive film situated at the base of said third cut-out thereby forming the bottom of said lower reservoir and capable of retaining liquid within said lower reservoir, and (iii) where the label of said first reagent is an enzyme, a predetermined amount of a third reagent comprising a substrate specific for said enzyme label to provide a chromogen indicative of the presence of said at least one analyte in said liquid sample; wherein said first, second and third films are superimposed and said first, second and third cut-outs coincide.

2. The device according to claim 1 wherein said first reagent is provided as a coating on the upper face of said first membrane.

3. The device according to claim 1 wherein the third reagent comprises cellulose pellets carrying the substrate.

4. The device according to claim 1 further comprising at least one additional set of cut-outs in said first, second and third films thereby forming at least one additional set of upper, median and lower reservoirs adapted to permit simultaneous detection of at least one additional analyte.

5. The device according to claim 1 further comprising a protective film covering the upper surface of said first film which covers said first reservoir until the device is used.

6. The device according to claim 5 wherein said at least one analyte is a member of a preselected group of analytes; the first reagent is a plurality of conjugates between (1) an enzyme label and (2) either each analyte in said preselected group or a corresponding antibody which specifically binds to each said analyte in said preselected group; and, the third reagent is a substrate specific for the enzyme label to provide a chromogen indicative of the presence of at least one member of the group or preselected analytes.

7. A device for detecting the presence of an antigen in a liquid sample comprising:
  (a) an upper reservoir capable of receiving said liquid sample comprising:
    (i) a first film having a first cut-out which defines the lateral walls of the upper reservoir for receiving said liquid sample,
    (ii) a first membrane comprised of gelatin and glass fibers situated at the base of said first cut-out thereby forming the bottom of said upper reservoir so as to retain said liquid sample in said upper reservoir for a predetermined period of time until contact with said liquid sample dissolves said gelatin, thereby permitting liquid in said upper reservoir to flow into a median reservoir, and
    (iii) a predetermined amount of a first reagent provided as a coating on the upper face of said first membrane, wherein said first reagent is an enzyme label conjugated to an antibody which specifically binds said antigen;
  (b) said median reservoir comprising:
    (i) a second film having a second cut-out which defines the lateral walls of said median reservoir positioned for receiving the upper reservoir liquid passing through said first membrane,
    (ii) a second membrane comprised of gelatin and glass fibers situated at the base of said second cut-out thereby forming the bottom of said median reservoir so as to retain said liquid in said median reservoir for a predetermined time until contact with said upper reservoir liquid dissolves said gelatin thereby permitting liquid in said median reservoir to flow into a lower reservoir, and
    (iii) a predetermined amount of a second reagent provided in said median reservoir, said second reagent selected from the group consisting of microspheres coated with said antigen and microspheres coated with said antibody;
  (c) said lower reservoir comprising:
    (i) a third film having a third cut-out which defines the lateral walls of said lower reservoir positioned for receiving said median reservoir liquid passing through said second membrane,
    (ii) a film situated at the base of said third cut-out thereby forming the bottom of said lower reservoir and capable of retaining liquid within said lower reservoir, and
    (iii) a predetermined amount of a third reagent provided in said lower reservoir comprising a substrate which develops a color reaction by contact with said enzyme label in the median reservoir liquid which reaches the lower reservoir after passing through the second membrane; wherein said first, second and third films are superimposed and said first, second and third cut-outs coincide.

8. A device according to claim 1 or claim 7, wherein said first, second and third films all have the same length and the same width.

9. A device according to claim 1 or claim 7, wherein said first film has a thickness from 0.5 mm to 5 mm.

10. A device according to claim 1 or claim 7, wherein said second film has a thickness from 1 mm to 5 mm.

11. A device according to claim 1 or claim 7, wherein said third film has a thickness from 0.5 mm to 2 mm.

12. A device according to claim 1 or claim 7, wherein said first and second membranes each have a thickness from 0.5 mm to 1.5 mm.

13. A device according to claim 1 or claim 7, wherein the glass fibers of said first and second membranes each form filters having a porosity from 0.2 to 50 microns.

14. A device according to claim 1 or claim 7, wherein said first membrane is sandwiched between said first and second films.

15. A device according to claim 1 or claim 7, wherein said second membrane is sandwiched between said second and third films.

16. A device according to claim 1 or claim 7, wherein said first membrane supports said first reagent on its upper face for reacting immediately with said liquid sample.

17. A device for detecting the presence of at least one analyte in a liquid sample comprising:
  (a) an upper reservoir for receiving said liquid sample comprising:
    (i) a first film from 0.5 to 5 mm thick having a first cut-out which defines the lateral walls of said upper reservoir,
    (ii) a first filter membrane from 0.5 to 1.5 mm thick comprised of gelatin and glass fibers situated at the base of said first cut-out thereby forming the bottom of said upper reservoir, wherein said first membrane is capable of retaining said liquid sample in said upper reservoir for a predetermined period of time until contact with said liquid sample dissolves said gelatin thereby permitting liquid in said upper reservoir to flow into a median reservoir through said glass fibers, said glass fibers providing a filter having a porosity of from about 0.2 to 50 microns, and
    (iii) a predetermined amount of a second reagent provided in said median reservoir suggested by said first membrane for reacting immediately with said liquid sample, said second reagent selected from the group consisting of (1) a conjugate of said at least one analyte and an enzyme, a fluorescent or a radioactive label, and (2) a conjugate of an antibody which specifically binds said at least one analyte and an enzyme, a fluorescent or a radioactive label;
  (b) said median reservoir comprising:
    (i) a second film from 1 to 5 mm thick having a second cut-out which defines the lateral walls of said median reservoir positioned for receiving the upper reservoir liquid filtering through said first membrane,
    (ii) a second filter membrane from 0.5 to 1.5 mm thick comprised of gelating and glass fibers situated at the base of said second cut-out thereby forming the bottom of said median reservoir, wherein said second membrane is capable of retaining said upper reservoir liquid in said medium reservoir for a predetermined period of time until contact with said upper reservoir liquid dissolves said gelatin thereby permitting liquid in said median reservoir to filter into a lower reservoir through said glass fibers, said glass fibers providing a filter having a porosity of from about 0.2 to 50 microns, and
    (iii) a predetermined amount of a second reagent provided in said median reservoir, said second reagent selected from the group consisting of microspheres coated with said at least one analyte and microsphere coated with said antibody; and (c) said lower reservoir comprising:
 (i) a third film from about 0.5 to 2 mm thick having a third cut-out which defines the lateral walls of said lower reservoir, and
 (iii) where the label of said first reagent is an enzyme, a predetermined amount of a third reagent comprising a substrate specific for said enzyme label to provide a chromogen indicative of the presence of said at least one analyte in said liquid sample;

wherein said first, second and third films we superimposed so said first, second and third cut-outs coincide.

18. A device according to claim 17, wherein said first, second and third films all have equal dimensions.

19. A device according to claim 17, wherein said first filter membrane is sandwiched between said first and second films, and wherein said second filter membrane is sandwiched between said second and third films.

20. A device according to claim 17, further comprising a protective adhesive film over said upper reservoir.

* * * * *